United States Patent [19]

Fukasawa et al.

[11] Patent Number: 4,857,308
[45] Date of Patent: Aug. 15, 1989

[54] COSMETIC POWDERS

[75] Inventors: Junichi Fukasawa, Yokohama; Haruya Kato, Funabashi; Katsumasa Iwaya, Oyama; Takako Shimizu, Tokyo; Atsushi Kawano, Sakura, all of Japan

[73] Assignee: Kao Corporation, Tokyo, Japan

[21] Appl. No.: 898,801

[22] Filed: Aug. 21, 1986

Related U.S. Application Data

[63] Continuation of Ser. No. 694,279, Jan. 24, 1985, abandoned.

[30] Foreign Application Priority Data

Feb. 6, 1984 [JP] Japan ................................ 59-19769

[51] Int. Cl.$^4$ .................... A61K 7/02; A61K 7/021; A61K 7/031; A61K 7/032
[52] U.S. Cl. .......................................... 424/63; 424/69
[58] Field of Search ................................ 424/69, 63

[56] References Cited

U.S. PATENT DOCUMENTS

| | | | |
|---|---|---|---|
| 2,938,901 | 5/1960 | Kerr et al. | 424/69 |
| 3,632,744 | 1/1972 | Paulsen | 424/69 |
| 4,474,818 | 10/1984 | Scott | 424/49 |

FOREIGN PATENT DOCUMENTS

| | | | |
|---|---|---|---|
| 498263 | 1/1951 | Belgium | 424/70 |
| 2000199 | 7/1971 | Fed. Rep. of Germany | 424/63 |
| 2708746 | 3/1978 | Fed. Rep. of Germany | 424/69 |
| 733444 | 10/1932 | France | 424/69 |
| 748236 | 6/1933 | France | 424/69 |
| 784404 | 4/1935 | France | 424/63 |
| 1057781 | 3/1954 | France | 424/69 |
| 406561 | 12/1943 | Italy | 424/69 |
| 0062220 | 4/1982 | Japan | 424/63 |
| 1126018 | 9/1968 | United Kingdom | 424/70 |

OTHER PUBLICATIONS

Chemical Abstracts, vol. 102, 1985, p. 36, Abstract No. 63078b, Columbus, Ohio, U.S.; & JP-A-59 170 131 (Daihachi Chemical Industry Co., Ltd.) 26-09-1984 *Abstract*.
The Fragrance Journal, vol. 2, No. 3, (1974) Colorant, 45, 593, (1972).
The Fragrance Journal, 30 (1978), p. 4.

*Primary Examiner*—Dale R. Ore
*Attorney, Agent, or Firm*—Oblon, Spivak, McClelland, Maier & Neustadt

[57] ABSTRACT

A cosmetic comprises an alkyl phosphate represented by the formula (I):

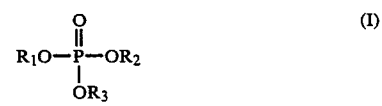

in which $R_1$ and $R_2$ independently represent hydrogen atom or an alkyl group having from 1 to 36 carbon atoms, and $R_3$ represents an alkyl group having from 1 to 36 carbon atoms, and a cosmetic powder.

The cosmetic is water-repellent in nature, unlikely to break by sweat and is readily spread on the skin with improved softness due to incorporation of the alkyl phosphate.

The cosmetic is prepared by first mixing the cosmetic powder and the alkyl phosphate dissolved in an organic solvent under heating conditions. Subsequently, the solvent is distilled off to form an alkyl phosphate coating on the indivisual particles. The coated particles are mixed with other cosmetic ingredients.

6 Claims, 1 Drawing Sheet

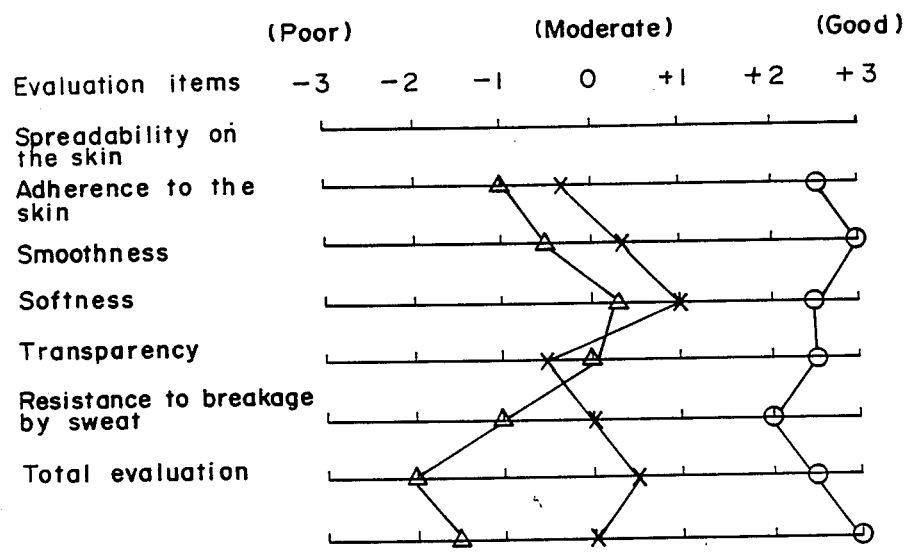

COSMETIC POWDERS

This application is a continuation of application Ser. No. 694,279, filed Jan. 24, 1985, now abandoned.

BACKGROUND OF THE INVENTION

1. Field of the Invention

This invention relates to the art of cosmetics and more particularly, to cosmetics which comprise alkyl phosphates and cosmetic powders by which the cosmetics are water-repellent in nature, are unlikely to suffer cosmetic breakage and are readily spread on the skin with improved softness.

2. Description of the Prior Art

At present, a number of cosmetics comprising cosmetic powders are commercially sold, including makeup cosmetics such as foundations, face powders, rouges, eye shadows, eye brows and the like, and body cosmetics such as body powders, baby powders and the like. The powders used in these cosmetics can be broadly divided into three groups including loading pigments, coloring pigments and composite pigments thereof. Of these pigments, loading pigments and composite pigments of loading and coloring pigments are used in relatively large amounts. Accordingly, the powder performances of these pigments give great influences on the performances of the respective cosmetics.

The cosmetic performances which are important as cosmetics comprising powders include spreading on the skin, smoothness, adherence and the like. With makeup cosmetics, cosmetic breakage is further added.

In order to improve these cosmetic performances, it is the usual practice to add cosmetic powders after coating thereon higher fatty acids, higher alcohols, fatty acid esters, metallic soaps and the like. In makeup cosmetics, there have been proposed several methods including a method (Japanese Laid-open Patent Application No. 54-14528) in which silicones having high water repellency are applied to powders in order to prevent the powder rom being wetted with water and thus prevent cosmetic breakage and also to allow use of these powders in cosmetics of water-containing and water-free types. Another method (Japanese Laid-open Patent Application No. 55-36213) includes use of powders which are treated, by baking, with silicone oils with or without containing other oils on the surface thereof.

However, these known methods have still drawbacks and are not satisfactory. More particularly, the surface coating method using higher fatty acids, higher alcohols, fatty acid esters and metalic soaps is disadvantageous in that clay minerals which are powder substrates used in cosmetics comprising powders are not imparted with water repellency. For instance, with pressed makeup cosmetics of the water-containing or water-free type, when the cosmetic is used while rubbing with water-containing sponge or puff on the surface thereof, "gloss" takes place, causing a problem of caking. On the other hand, when silicones are added to make, for example, pressed makeup cosmetics, it is difficult to mold even when the compression pressure is raised with an attendant disadvantage that the powder itself is felt very rough.

SUMMARY OF THE INVENTION

The present inventors have intensive studies to obtain powder-containing cosmetics which are free of the above disadvantages and have good cosmetic performances. As a result, it was found that cosmetics to which a specific type of alkyl phosphate and a cosmetic powder were added had high water repellency and no roughness. Thus, smoothness and softness on the skin were remarkably improved and when press molded, such cosmetics had good shape retentivity. The present invention is accomplished based on the above finding.

According to the present invention, there is provided a cosmetic which comprises an alkyl phosphate represented by the following general formula (I)

in which $R_1$ and $R_2$ independently represent hydrogen atom or an alkyl group having from 1 to 36 carbon atoms, and $R_3$ represents an alkyl group having from 1 to 36 carbon atoms.

BRIEF DESCRIPTION OF THE DRAWINGS

A sole FIGURE is a graph showing the results of organoleptic evaluation of powder foundations using dicetyl phosphate-coated sericite, non-treated sericite and methylhydrogen polysiloxane-coated sericite.

DETAILED DESCRIPTION OF THE INVENTION AND PREFERRED EMBODIMENTS

The alkyl phosphates represented by the formula (I) are known compounds. The alkyl groups represented by $R_1$ to $R_3$ may be either saturated or unsaturated and linear or branched. Specific examples of the alkyl groups include saturated alkyl groups such as methyl, ethyl, propyl, butyl, amyl, hexyl, heptyl, octyl, nonyl, decyl, lauryl, myristyl, cetyl, stearyl, behenyl and the like, and unsaturated alkyl groups such as ethenyl, propenyl, butenyl, pentenyl, hexenyl, octenyl, nonenyl, decynyl, oleyl, eicosynyl and the like. Of these alkyl phosphates, dialkyl phosphates of the following formula (II):

in which $R_4$ and $R_5$ independently represent a linear alkyl group having 14 to 22 carbon atoms are preferred.

The cosmetic powders may be powders ordinarily used for these purposes and include, for example, inorganic loading pigments such as talc, clay minerals such as sericite, mica, kaolin, Ilite, acidic terra alba, bentonite and the like, organic loading pigments such as nylons, polyethylene, silk powder and the like, inorganic pigments such as titanium oxide, zinc oxide, ultramarine blue, chromium oxide, iron oxide and the like; organic pigments such as organic tar pigments, lakes and the like, and composite pigments such as titanium dioxide-coated mica, iron oxide-coated mica and the like. These powders may be used singly or in combination. Of these cosmetic powders, inorganic powders such as talc, clay minerals which contain Al atoms, titanium dioxide coated mica, iron oxide-coated mica and the like are preferred when applied as body cosmetics.

In order to prepare cosmetics, alkyl phosphates and cosmetic powders may be mixed with other arbitrary ingredients by means of a Henschel mixer, a Nauta mixer, a ribbon blender or mortar. In order to further improve water repellency, it is preferable to first mix cosmetic powders and alkyl phosphates such as in a mortar sufficiently to permit them compatible with each other, followed by mixing with other ingredients.

It is also preferred that alkyl phosphates are dissolved in organic solvents such as benzene, toluene, acetone and the like under heating conditions, to which cosmetic powders are added and agitated. Thereafter, the solvent is distilled off to form an alkyl phosphate coating on the individual particles. The coated particles are mixed with other ingredients.

The mixing temperature is 20° to 90° C., and preferably 40° to 80° C. Amount of organic solvent is 0.3 to 30 times, and preferably 0.5 to 10 times as large as the amount of inorganic powder based on a weight proportion. The mixing time depends on the treating amount, sort of the inorganic powder, etc., but generally the time is 1 to 15 hours, and preferably, 2 to 10 hours.

It will be noted that after the coating, the powder may be heated to a level higher than a melting point of the alkyl phosphate in order to cause the powders compatible with the alkyl phosphate. Prior to coating with the alkyl phosphate dissolved in organic solvents, the cosmetic powder may be pretreated as follows; the powder is calcined at 110° C. for 30 minutes to 80 hours under reduced pressure to dry the powder whereby water repellency after the coating is much improved. In the coating treatment, two or more types of cosmetic powders may be used at the same time. Within ranges of amounts not impeding the effects of the present invention, other known coating materials such as silicones, higher fatty acids, higher alcohols, esters and waxes may be used for the coating.

In the practice of the invention, the amount of alkyl phosphate depends on the type and is generally in the range of 0.1 to 50 wt % (hereinafter referred to simply as %), preferably 2 to 20%, of the cosmetic powder. If the alkyl phosphate is too small, water repellency becomes unsatisfactory, whereas too large amounts may result in a loss of spreadability of loading pigments themselves.

The cosmetics of the invention include makeup cosmetics such as foundations, rouges, eye shadows, eye brows and the like; and body cosmetics such as body powders, baby powders and the like. For the preparation of these cosmetics, there may be further used, aside from cosmetic powders, oils such as higher fatty acids, high alcohols, waxes, esters, hydrocarbons, silicones and the like. If necessary, antiseptics, antioxidants, perfumes, astringents and the like. With eye shadows, rouges and similar cosmetics, it is possible to add loading pigments. However, in order to obtain cosmetics having good water repellency, it is preferable to coat not only the loading pigments, but also color pigments such as titanium oxide, zinc oxide, ultramarine blue, chromium oxide, iron oxide and organic tar pigments.

The thus obtained cosmetics of the present invention are imparted with water repellency from alkyl phosphates and have not only good spreadability, softness and smoothness on the skin, but also are resistant to sweat and water. When the cosmetics are pressed powdery makeup cosmetics such as foundations, eye shadows, rouges and the like, the cosmetic composition of the invention is readily press molded as desired without involving breakage of the cosmetic spread on the skin.

The present invention is described in detail by way of examples.

EXAMPLE 1

Talc (Talc JA 46R; manufactured by Asada Seifun Ltd.) was provided as a cosmetic powder and was mixed or coated with a number of alkyl phosphates to determine water repellency.

Mixing method: 0.1–2 g of alkyl phosphates and 10 g of talc were mixed in an automatic mortar (automatic mortar Model NMW 200W, by Nitto Co., Ltd.) for 30 minutes to 4 hours.

Coating method: 0.1–2 g of alkylphosphates and 100 ml of hexane were placed in a 300 milliliter egg plant-type flask and agitated at 50° C. for about 20 minutes. Thereafter, 10 g of talc was added and the egg plant-type flask was rotated for about 30 minutes without sucking with a rotary evaporator, followed by distilling off the hexane at 60° C. under suction with a tap aspirator. The resulting powder was dried overnight under reduced pressure at 50° C. to completely remove the hexane therefrom.

About 0.05 g of the powder thus obtained was floated on 15 ml of water in a 30 ml beaker, which was then shaken to visually observe dispersability of the powder in water. For control, the above procedure was repeated using non-treated talc.

Evaluation was effected as follows.

0: powder was immediately dispersed in water.

1: when the beaker was shaken, almost all powder was dispersed in water within 30 seconds.

2: When the beaker was shaken, water became turbid after 30 seconds but floating powder was also observed.

3: When the was shaked, water became turbid after 1 minute and the powder floated on the water was recognized in relatively large amounts.

4: When the beaker was shaked, the water did not become turbid even after 1 minute, but no powder dispersed in the water was recognized.

5: When the beaker was shaked over 1 minutes, no powder was found to be dispersed in water.

The results are shown in Table 1 below.

TABLE 1

| Alkyl Phosphate | Coating Method | | Mixing Method | |
| --- | --- | --- | --- | --- |
| | Treating Amount (wt %) | Water Repellency | Treating Amount (wt %) | Water Repellency |
| Comparison | | | | |
| Non-treated Product | — | 1 | — | 1 |
| Products of Invention | | | | |
| Dioctyl Phosphate | 2 | 2 | 2 | 1–2 |
| " | 5 | 3 | 5 | 1–2 |
| Dilauryl Phosphate | 2 | 3 | 2 | 2 |
| " | 5 | 3–4 | 5 | 2 |
| Dicetyl Phosphate | 2 | 3–4 | 2 | 2 |
| " | 5 | 4–5 | 5 | 2 |
| " | 10 | 5 | 10 | 2 |
| " | 20 | 5 | 20 | 2 |
| Distearyl Phosphate | 2 | 3–4 | 2 | 2 |
| " | 5 | 5 | 5 | 2 |
| Dibehenyl Phosphate | 2 | 4 | 2 | 2 |
| " | 5 | 5 | 5 | 2 |
| Dioleyl Phosphate | 2 | 4 | 2 | 2 |
| " | 5 | 5 | 5 | 2 |
| Monostearyl Phosphate | 5 | 2 | 5 | 1–2 |
| Tristearyl Phosphate | 5 | 3 | 5 | 1–2 |

EXAMPLE 2

Sericite (Sericite SP; manufactured by Horie Kako K.K.) was provided as the cosmetic powder. Sericite was dried at 110° C. under reduced pressure overnight, after which it was mixed or coated with various alkyl phosphates in the same manner as in Example 1. The resulting powders were tested to determine water repellency according to the method of Example 1. Moreover, a bonding force of each powder which is an index to shape retentivity of the powder was determined by a procedure in which 2 g of the powder was shaped as tablets having a diameter of 2 cm under a pressure of 200 Kg/cm$^2$ and was compressed by means of a rheometer, made by Fudo Ind. Co., Ltd., to determine a force (Kg) required for breakage of the tablet. A resistance to abrasion (friction factor) which is an index to smoothness of powder was checked by the use of a surface tester HEIDON-14, by Shinto Science Co., Ltd.

The amount of each alkyl phosphate was 10% of the powder. For control, non-treated sericite was used. The results are shown in Table 2.

TABLE 2

| Alkyl Phosphate | Coating Method | | | Mixing Method | | |
|---|---|---|---|---|---|---|
| | Water Repellency | Binding Force | Friction Factor | Water repellency | Binding Force | Friction Factor |
| Comparison | | | | | | |
| Non-Treated | 0 | 0.62 Kg | $1.7 \times 10^{-2}$ | 0 | 0.62 Kg | $1.7 \times 10^{-2}$ |
| Products of Invention | | | | | | |
| Dilauryl Phosphate | 4 | 1.27 Kg | $1.2 \times 10^{-2}$ | 1 | 1.10 Kg | $1.2 \times 10^{-2}$ |
| Dicetyl Phosphate | 5 | 1.44 Kg | $1.0 \times 10^{-2}$ | 1 | 1.37 Kg | $1.1 \times 10^{-2}$ |
| Distearyl Phosphate | 5 | 1.52 Kg | $1.1 \times 10^{-2}$ | 1 | 1.41 Kg | $1.2 \times 10^{-2}$ |
| Monostearyl Phosphate | 2 | 1.20 Kg | $1.0 \times 10^{-2}$ | 1 | 1.15 Kg | $1.1 \times 10^{-2}$ |
| Tristearyl Phosphate | 3 | 1.53 Kg | $1.2 \times 10^{-2}$ | 1 | 1.44 Kg | $1.2 \times 10^{-2}$ |

EXAMPLE 3

Ten grams of sericite (Sericite SL; manufactured by Horie Kako K.K.) was coated with 1 g of an alkyl phosphate or an oil in the same manner as in Example 3 and water repellency and abrasion resistance of the resulting powders were determined. The results are shown in Table 3 below.

TABLE 3

| Products of Invention | | | Comparative Products | | |
|---|---|---|---|---|---|
| Coating Material | Water Repellency | Friction Factor | Coating Material | Water Repellency | Friction Factor |
| Dilauryl Phosphate | 4 | $1.2 \times 10^{-2}$ | Lauric Acid | 2 | $1.4 \times 10^{-2}$ |
| Dicetyl Phosphate | 5 | $1.0 \times 10^{-2}$ | Palmitic Acid | 2 | $1.4 \times 10^{-2}$ |
| Distearyl Phosphate | 5 | $1.1 \times 10^{-2}$ | Stearic Acid | 2 | $1.4 \times 10^{-2}$ |
| | | | Paraffin Wax 140° F. | 1–2 | $1.8 \times 10^{-2}$ |
| | | | Lanoline Fatty Acid | 3 | $1.6 \times 10^{-2}$ |
| | | | Candelilla Wax | 3–4 | $1.6 \times 10^{-2}$ |

Thus, as different from ordinary oils, alkyl phosphates can impart very specific water repellency and smoothness to cosmetic powders.

EXAMPLE 4

Sericite (Sericite FSE; manufactured by Sanshin Koko K.K.) which was coated with 7% of distearyl phosphate in the same manner as in Example 1 (hereinafter referred to as sample (A)) was used to make a pressed face powder having the following formulation.

Formulation of Face Powder (Formulation 1):
 magnesium stearate: 1.2(%)
 liquid paraffin: 3.0
 silicone oil: 2.0
 titanium oxide: 1.5
 red iron oxide: 0.15
 yellow iron oxide: 0.1
 black iron oxide: 0.01
 perfume: 0.5
 sample (A): 91.54

This face powder was used by 10 female panelers in ordinary manner and was evaluated with respect to spreadability on the skin, smoothness, softness and compatibility with the skin. For comparison, formulation 1 was also prepared using nontreated sericite (Formulation 2). The results are shown in Table 4 below.

TABLE 4

| Formulation No. | Spreadability | Smoothness | Softness | Compatibility |
|---|---|---|---|---|
| 1 | 9 | 10 | 9 | 10 |
| 2 | 1 | 0 | 1 | 0 |

EXAMPLE 5

Sericite (Sericite SL; manufactured by Horie Kako K.K.) which was coated with 10% of dipalmityl phosphate as in Example 3 (hereinafter referred to as sample (B)) was used to prepare a powder foundation according to the following formulation.

Formulation of Powder Foundation (Formulation 3):
 liquid paraffin: 5.0(%)
 lanolin: 2.0
 isopropyl myristate: 1.0
 titanium oxide: 7.0
 red iron oxide: 0.8
 yellow iron oxide: 1.0
 black iron oxide: 0.07
 perfume: 0.3
 sample (B): 82.83

The powder foundation was organoleptically evaluated by 20 female panelers. For comparison, formulation (3) was prepared using non-treated sericite instead of sample (B) (formulation 4) and, instead of sample (B), sericite coated with 2% methylhydrogen siloxane ordinarily used for these purposes (formulation 5):

The results are shown in FIG. 1, in which o—o indicates formulation 3, △—△ indicates formulation 4 and x—x indicates formulation 5.

EXAMPLE 6

Commercially available titanium dioxide-coated mica (Coloron light blue, by Merck & Inc.) was provided as a cosmetic powder and coated with 10% of dipalmityl phosphate according to the procedure of Example 1 (sample (C)). The sample (C) was used to make an eye shadow of the pressed powder type having the following formulation. The compression pressure used was 30 Kg/cm$^2$. Formulation of Eye Shadow (Formulation 6):
sample (C): 99.7%
perfume: 0.3

For comparison, non-treated titanium dioxide-coated mica was used to make the pressed powder-type eye shadow (formulation 7), but press molding was impossible.
Formulation 7:
coloron light blue: 69.7–94.7(%)
squalane: 5–30
perfume: 0.3

EXAMPLE 7

75 g (or 30 g, 150 g) of dicetyl phosphate and 3000 g of n-hexane were placed in a kneader (manufactured by Satake Kagaku Kikai K.K.), and heated to 60° C. while kneading, to which 1500 g of sericite SL (manufactured by Horie Kako K.K., acidic point=$2.5 \times 10^{-5}$ mol/g for $H_0$ of $+1.2$ or less, and acidic point=$2.6 \times 10^{-5}$ mol/g for $H_0$ of $+3.3$ or less) was charged and mixed for 4 hours at 60° C. Thereafter, the n-hexane was distilled off at 50° to 60° C. under reduced pressure for 2 hours. The resulting powder was dried to obtain 1560 g (or 1520 g, 1630 g) of dried powder.

EXAMPLE 8

The process of Example 7 was followed using 75 g (or 30 g) of distearyl phosphate, 1500 g of n-hexane and 1500 g of sericite SP (manufactured by Horie Kako K.K., acidic point=$2.5 \times 10^{-5}$ mol/g for $H_0$ of $+1.2$ or less, and acidic point=$2.5 \times 10^{-5}$ mol/g for $H_0$ of $+3.3$ or less), thereby obtained 1565 g (or 1530 g) of a powder.

EXAMPLE 9

The process of Example 7 was followed using 75 g (or 30 g) of dicetyl phosphate, 3000 g of n-hexane and sericite SL which was previously mixed with water (manufactured by Horie Kako K.K., water content in a dried state=0.7 wt %), thereby obtained 1560 g (or 1520 g) of a powder.

EXAMPLE 10

Powder obtained in Examples 7, 8 and 9 were tested to determine water repellency and resistance to abrasion which is an index to smoothness of powder, according to the methods of Examples 1 and 2. The results are shown in Table 5.

TABLE 5

| Tested Material | Dialkyl Phosphate* (wt %) | Water Repellency | Friction Factor |
| --- | --- | --- | --- |
| Sericite SL | — | 0 | $1.8 \times 10^{-2}$ |
| Talc | — | 1 | $1.7 \times 10^{-2}$ |
| Powder of Example 7 | 2 | 4 | $1.2 \times 10^{-2}$ |
| | 5 | 4–5 | $1.0 \times 10^{-2}$ |
| | 10 | 5 | $1.1 \times 10^{-2}$ |
| Powder of Example 8 | 2 | 4 | $1.1 \times 10^{-2}$ |
| | 5 | 5—5 | $1.1 \times 10^{-2}$ |
| Powder of Example 9 | 2 | 4–5 | $1.2 \times 10^{-2}$ |
| | 5 | 5 | $1.0 \times 10^{-2}$ |

*Treating amount of dialkyl phosphate to amount of clay minerals (wt %)

As will be seen from the data of Example 10, inorganic powders which are surface-treated according to Examples 7 to 9 exhibit excellent water repellency and feel of smoothness, and thus useful as a cosmetic powder.

What is claimed is:

1. A make-up cosmetic or a body cosmetic selected from the group consisting of body powder and baby powder of improved water repellence and improved softness to the skin, which comprises:
a cosmetic powder selected from the group consisting of particles of inorganic loading pigments and composite pigments, said cosmetic powder particles being coasted by an amount of from 0.1 to 50 wt. % of a dialkyl phosphate of the formula:

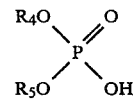

where $R_4$ and $R_5$ independently each represent a linear alkyl group having from 14 to 22 carbon atoms.

2. The cosmetic according to claim 1, wherein said cosmetic powder is an inorganic loading pigment selected from the group consisting of talc, sericite, mica, kaolin, Ilite, acidic terra abla, bentonite, or a composite pigment selected from the group consisting of titanium dioxide-coated mica and iron oxide-coated mica.

3. The cosmetic according to claim 1, wherein said linear alkyl group is myristyl, cetyl, stearyl, behenyl, oleyl, or eicosynyl.

4. The cosmetic according to claim 1, wherein the amount of said dialkyl phosphate employed ranges from 2 to 20% by weight.

5. A make-up cosmetic or a body cosmetic selected from the group consisting of body powder and having baby powder of improved water repellence and improved softness to the skin, which comprises:
a cosmetic powder selected from the group consisting of particles of inorganic loading pigments and composite pigments, said cosmetic powder particles being coated by an amount of from 0.1 to 50 wt. % of a dialkyl phosphate of the formula:

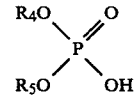

wherein $R_4$ and $R_5$ independently each represent a linear alkyl group having from 14 to 22 carbon atoms, wherein coating of said dialkyl phosphate on said cosmetic powder particles is effected by adding said cosmetic powder particles to an organic solvent solution of a dialkyl phosphate and removing said organic solvent by distillation.

6. The cosmetic according to claim 5, wherein said organic solvent is selected form the group consisting of hexane, benzene, toluene and acetone.

* * * * *